United States Patent [19]

Baiocchi et al.

[11] 4,134,989
[45] Jan. 16, 1979

[54] GUAIACOL p-ISOBUTYL HYDRATROPATE

[75] Inventors: Leandro Baiocchi; Bruno Silvestrini, both of Rome, Italy

[73] Assignee: Aziende Chimiche Riunite Angelini Francesco A.C.R.A.F. S.p.A., Rome, Italy

[21] Appl. No.: 809,833

[22] Filed: Jun. 24, 1977

[30] Foreign Application Priority Data

Jul. 9, 1976 [IT] Italy .................. 25174 A/76

[51] Int. Cl.² .................................... C07C 69/76
[52] U.S. Cl. ............................. 424/308; 560/105
[58] Field of Search ........... A61K/31/235; 560/105; 424/308

[56] References Cited

U.S. PATENT DOCUMENTS

| 3,452,079 | 6/1969 | Shen et al. | 560/105 |
| 4,016,197 | 4/1977 | Baiocchi | 560/105 |

OTHER PUBLICATIONS

Groggins, Unit Processes in Organic Synthesis, 4th Edition, pp. 623–624 (1952).

Primary Examiner—Jane S. Myers
Attorney, Agent, or Firm—Ladas, Parry, Von Gehr, Goldsmith & Deschamps

[57] ABSTRACT

This invention provides guaiacol p-isobutyl hydratropate as a new compound for use in human therapy as an analgesic, anti-inflammatory, antipyretic, antiseptic and expectorating agent.

2 Claims, No Drawings

GUAIACOL P-ISOBUTYL HYDRATROPATE

The present relates to guaiacol pisobutyl hydratropate (I)

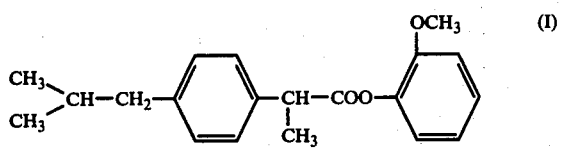

and a process for its preparation. (I) is endowed with analgesic, antiflammatory, antipyretic, antiseptic and expectorating activity on laboratory animals. Due to its low toxicity and to its wide spectrum of pharmacological utilization, its use in human therapy can be foreseen for inflammatory conditions of the respiratory tract (acute and chronic bronchitis, etc.) at daily doses in the range of 0.5–2.5 g.

The experimental study of guaiacol para-isobutylhydratropate (GIH) dealt with the following aspects:

1. Acute toxicity: The experiments were aimed at determining the $LD_{50}$ of GIH in comparison with ibuprofen. Long-Evans rats of both sexes were used weighing 135–188 grams. The drugs were suspended in methyl-cellulose (0.5%) and given by gavage. Deaths were recorded during the two weeks following treatment. The $LD_{50}$ was calculated according to Litchfield and Wilcoxon (1949). LITCHFILED J. T. and WILCOXON F. A., A simplified method for evaluating dose-effect experiments. J. Pharmacol. Exp. Ther. 96, 99, 1949. The results obtained are given in Table I. The results obtained show that GIH is definitely less toxic than ibuprofen.

TABLE I

| | $LD_{50}$ of guaiacol p. isobutyl-hydratropate and ibuprofen in rats. | | |
|---|---|---|---|
| Drug | No. of animals | $LD_{50}$ and confidential limits | S |
| GIH | 38 | 1650 (1246–2185) | 1.93 |
| Ibuprofen | 42 | 640 (509–805) | 1.42 |

2. Gastrointestinal tolerance: In these experiments also GIH was compared to ibuprofen in order to assess whether it was better tolerated at the level of the gastrointestinal tract. In fact, it is well known that one of the most important limits to the therapeutic use of drugs having antiinflammatory properties is their ability to produce erosions or ulcers of the gastrointestinal tract.

Experiments were done in Long-Evans rats of both sexes weighing 150–190 grams. The drugs were suspended in methyl-cellulose (0.5%) and given by gavage. The animals were fasted during the 8 hours before treatment and were sacrificed 18 hours later. They were autopsied and gastrointestinal lesions were scored according to the score system described by Cioli et al. (1967). CIOLI V., SILVESTRINI B., and DORDONI F., Evaluation of the potential of gastric ulceration after administration of certain drugs. Exp. molec. Path. 6, 68–83, 1967. The effects of the two drugs under investigation on the gastric mucosa are given in Table II. The results obtained show that GIH is less toxic than ibuprofen.

Similar results were obtained with regard to intestinal lesions; the results obtained are given in Table III. In essence these results show that GIH maintains the gastrointestinal toxicity which is typical of anti-inflammatory drugs but is less toxic than ibuprofen.

3. Anti-inflammatory activity: In connection with the anti-inflammatory activity, both the anti-edema and analgesic activities were studied (namely, the ability to inhibit the painful response from inflamed tissues). The anti-edema activity was studied according to Winter et al. (1962). WINTER C. A., RISLEY E. A. and NUSS G. W., Carrageenin-induced edema in hind

TABLE II

| Ulcerogenic activity of GIH and Ibuprofen in the gastric muscosa of rats. | | | |
|---|---|---|---|
| Drug | Dose mg/kg p.o. | No. of rats | % of rats with ulcers |
| GIH | 25 | 10 | 0 |
| | 38 | 10 | 10 |
| | 112 | 30 | 33 [2] |
| Ibuprofen | 16 | 10 | 11 |
| | 25 | 15 | 33 [3] |
| | 75 | 30 | 43 [1] |

Significance with respect to the controls:
[1] = $P < 0.001$
[2] = $P < 0.01$
[3] = $P < 0.05$

TABLE III

| Ulcerogenic activity of GIH and Ibuprofen on the intestine of rats. | | | |
|---|---|---|---|
| Drug | Dose mg/kg p.o. | No. of rats | % of rats with ulcers |
| GIH | 25 | 10 | 0 |
| | 38 | 10 | 20 |
| | 112 | 30 | 33 [2] |
| Ibuprofen | 16 | 10 | 0 |
| | 25 | 15 | 20 |
| | 75 | 30 | 63 [1] |

Significance with respect to the controls:
[1] = $P < 0.001$
[2] = $P < 0.01$ paw of the rat as an assay for anti-inflammatory drugs. Proc. Soc. Exp. Biol. Med. 111, 544–547, 1962.

Experiments were done on Long-Evans rats of both sexes weighing 150–190 grams. The analgesic activity was studied according to Hendershot and Forsaith (1959). HENDERSHOT L. C. and FORSAITH J., Antagonism of the frequency of phenylquinone induced writhing in the mouse by weak analgesics and non-analgesics. J. Pharmacol. Exp. Ther. 125, 237–240, 1959. Swiss mice of both sexes weighing 18–22 grams were used. Both in the rats and mice the drugs were suspended in methyl-cellulose (0.5%) and given by gavage.

The effects on GIH and ibuprofen on carrageenin edema are given in Table IV. In this test the two drugs revealed substantially the same anti-inflammatory activity. The results dealing with the analgesic activity are presented in Table V. The two drugs showed a similar trend of effects.

4. Effects on the respiratory system: The specific therapeutic value of GIH was assessed by the following experiments; test of anti-tussive activity; pharmacokinetic studies.

The test for the anti-tussive activity was done according to Silvestrini and Pozzatti (1960) SILVESTRINI B. and POZZATTI C., Anti-tussive activity and other pharmacological properties of six oxadiazoles. Arch. int. pharmacodyn. 129, 249–263, 1960. Since the details are given in this publication, it should only be recalled that the test is performed on guineapigs by using acrolein inhalation to produce cough. Male guinea pigs were used weighing 300–500 grams. The pharmacokinetic study was performed in Long-Evans rats of both sexes weighing 150 grams. GIH was suspended in methyl-cellulose (0.5%) and given by gavage. The animals were sacrificed at

TABLE IV

Effects of GIH and Ibuprofen on carrageenin-induced paw edema in rats.

| Drug | Dose mg/kg p.o. | No. of rats | Reduction of edema at the following times: | | |
|---|---|---|---|---|---|
| | | | 2 hours | 4 hours | 6 hours |
| GIH | 1.9 | 20 | 22 (3) | 12 (4) | 1 |
| | 3.8 | 30 | 33 (1) | 26 (1) | 17 (3) |
| | 7.5 | 10 | 41 (2) | 28 (2) | 27 |
| | 15 | 15 | 50 (1) | 45 (1) | 43 (1) |
| Ibuprofen | 2.5 | 31 | 17 | 15 (3) | 3 |
| | 5 | 15 | 41 (1) | 31 (1) | 26 (2) |
| | 10 | 16 | 57 (1) | 47 (1) | 36 (1) |

Significance with respect to the controls:
(1) = P<0.001
(2) = P<0.01
(3) = P<0.02
(4) = P<0.05

TABLE V

Effects of GIH and Ibuprofen on the writhing reflexes induced by phenylquinone in rats.

| Drug | Doses mg/kg p.o. | No. of mice | % reduction in number of writhings |
|---|---|---|---|
| GIH | 1.9 | 18 | 11 |
| | 3.8 | 21 | 28 (2) |
| | 7.5 | 15 | 37 (2) |
| | 15 | 15 | 43 (1) |
| | 30 | 12 | 55 (1) |
| Ibuprofen | 5 | 15 | 18 |
| | 10 | 15 | 46 (1) |
| | 20 | 12 | 52 (1) |

Significance with respect to the controls:
(1) = P<0.001
(2) = P<0.01 time intervals and serum samples were taken. GIH was dosed according to the method of Mizutani and Naito (1967) adapted to GIH. MIZUTANI M. and NAITO S., Studies on absorption and excretion of drugs. XXIX. Biopharmaceutical studies on guaiacol glycerol ether and related compounds. I. Blood level of guaiacol glycerol ether in rabbit and its binding with serum proteins. Chem. Pharm. Bull. 15, 1422–1426, 1967. Moreoever, ibuprofen and guaiacol were dosed according to the methods of Kaiser and Vangiessen (1974) and Mizutani and Naito (1967), respectively. KAISER, D. G. and VANGIESSEN G. J., GLC determination of ibuprofen [(+)-2-(p-isobutylphenyl)propionic acid] in plasma. J. Pharm. Sci. 63, 219–221, 1974. MIZUTANI M. and NAITO S., Studies on absorption and excretion of drugs. XXIX. Biopharmaceutical studies on guaiacol glycerol ether and related compounds. I. Blood level of guaiacol glycerol ether in rabbit and its binding with serum proteins. Chem. Pharm. Bull. 15, 1422–1426, 1967.

In the test for the anti-tussive activity GIH was compared to codein. Both compounds turned out to be active and the minimal effective dose was 25 mg/kg p.o. and 2.5 mg/kg i.p., respectively. The pharmacokinetic studies failed to demonstrate the presence of GIH in the blood following oral administration. This fact is explained by the observation that GIH is rapidly hydrolyzed into ibuprofen and guaiacol in the presence of serum. It should also be mentioned that no hydrolysis occurs in the presence of artificial gastric juices. Therefore, it is concluded that hydrolysis most probably occurs after absorption. Both ibuprofen and guaiacol have instead been found in the serum samples taken from rats treated with GIH.

5. Comments: On the whole these experiments provided the following information: (1) GIH possesses a low general and gastro-intestinal toxicity. (2) GIH possesses antiinflammatory and anti-tussive properties which are of therapeutic value in inflammatory conditions of the respiratory tract. (3) GIH following oral administration is broken-down into ibuprofen and guaiacol. The anti-inflammatory effects of GIH may therefore be attributed to ibuprofen, whereas guaiacol may produce its well known pharmacological effects such as expectorant and anti-septic effect. On the basis of the results obtained it is also suggested that the better tolerance of GIH, with respect to ibuprofen, is due to the fact that ibuprofen is released following oral absorption; therefore, GIH avoids the local irritating effects of ibuprofen on gastric mucosa while preserving at the same time the pharmacological action of guaiacol.

According to the present invention, (I) is prepared starting from p-isobutyl-hydratropoly chloride and guaiacol in presence of an acid catalyst (HCl, $H_2SO_4$, p-toluenesulfonic acid, etc.). More conventional and different preparations of the compound itself have been attempted but they have all been found not very interesting from the practical standpoint and for their low yields (action of p-isobutyl-hydratropoyl chloride on sodium guaiacol) or for the too many passages (transesterification of a p-isobutyl-hydratropic acid ester or metilation of the hydroxy derivative corresponding to (I)).

The following, non limitative example, illustrates the invention:

EXAMPLE I

A mixture containing p-isobutyl-hydratropoyl chloride (21.5g), guaiacol (8.4g) and a drop of conc. $H_2SO_4$ is stirred for 24 hours at room temperature, then for further 30 min. in a water bath. After cooling the mixture is extracted with ether and washed with a solution of sodium bicarbonate and then with water. The residue obtained after removal of the solvent is distilled. b.p. 190° C./0.5 mm/Hg. Yield 21g.

On standing the product crystallizes. m.p. 35–36° C.
NMR (CDCl$_3$, TMS as internal standard) spectrum:
Multiplet between 6.70 and 7.50 δ (8H) (aromatic protons)
Quartet centered at 3.95 δ (1H) Ar-CH-CH$_3$
Singlet at 3.60 δ (3H)-OCH$_3$
Doublet centered at 2.46 δ (2H) Ar-CH$_2$-CH
Doublet centered at 1.57 δ (3H) CH$_3$-CH
Multiplet between 1.5 and 2.2 δ

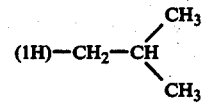

Doublet centered at 0.90 δ

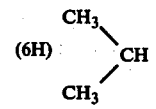

I.R. Spectrum (film) ν C=O = 1760 cm$^{-1}$

We claim:
1. Guaiacol p-isobutyl hydratropate of the formula
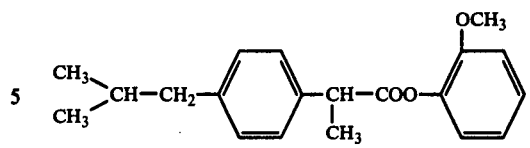
2. A process for the treatment of inflammatory conditions of the respiratory tract of a human comprising the administration to said human of guaiacol p-isobutyl hydratropate of the formula I as defined in claim 1 at a daily dose in the range of 0.5 to 2.5 g.
* * * * *